United States Patent
Kandasami et al.

(10) Patent No.: US 10,645,888 B2
(45) Date of Patent: May 12, 2020

(54) REGENERATION AND GENETIC TRANSFORMATION OF OKRA THROUGH SOMATIC EMBRYOGENESIS

(71) Applicant: RASI SEEDS PRIVATE LIMITED, Coimbatore, Tamil Nadu (IN)

(72) Inventors: Poovannan Kandasami, Vellore (IN); Sabaripriya Ravindran, Nanded (IN); Mohanraj Perumal, Namakkal (IN); Manonmani Elangovan, Salem (IN); Packialakshmi Maruthayee Rajendran, Madurai (IN); Saravanakumar Marappan, Coimbatore (IN); Subramanian Vaidyanathan, Hyderabad (IN); Ramasami Muthugounder, Salem (IN)

(73) Assignee: RASI SEEDS PRIVATE LIMITED, Coimbatore, Tamil (IN)

( * ) Notice: Subject to any disclaimer, the term of this patent is extended or adjusted under 35 U.S.C. 154(b) by 147 days.

(21) Appl. No.: 15/573,134

(22) PCT Filed: Jan. 27, 2016

(86) PCT No.: PCT/IN2016/000030
§ 371 (c)(1),
(2) Date: Nov. 10, 2017

(87) PCT Pub. No.: WO2016/189543
PCT Pub. Date: Dec. 1, 2016

(65) Prior Publication Data
US 2018/0116143 A1    May 3, 2018

(30) Foreign Application Priority Data
May 25, 2015   (IN) ............................ 2617/CHE/2015

(51) Int. Cl.
*A01H 4/00* (2006.01)
*C12N 5/00* (2006.01)

(52) U.S. Cl.
CPC ............ *A01H 4/005* (2013.01); *A01H 4/001* (2013.01); *A01H 4/008* (2013.01); *C12N 5/0025* (2013.01)

(58) Field of Classification Search
None
See application file for complete search history.

(56) References Cited

U.S. PATENT DOCUMENTS

| | | | |
|---|---|---|---|
| 8,067,673 B2 | 11/2011 | Zehr et al. | |
| 8,168,748 B2 | 5/2012 | Hanley-Bowdoin et al. | |
| 8,697,445 B2 | 4/2014 | Zehr et al. | |
| 2002/0083491 A1 | 6/2002 | Peele et al. | |
| 2007/0266460 A1* | 11/2007 | Wilkins | A01H 4/008 800/294 |

FOREIGN PATENT DOCUMENTS

WO    2011087854    7/2011

OTHER PUBLICATIONS

Sharma et al. (World Journal of Agricultural Sciences 4.4 (2008): 449-452). (Year: 2008).*
Cook, D. A., and A. Brown. "Somatic embryogenesis and organogenesis in okra (*Abelmoschus esculentus* L. Moench.)." Somatic Embryogenesis and Synthetic Seed II. Springer, Berlin, Heidelberg, 1995. 164-169. (Year: 1995).*
Rahman et al. (Journal of Bio-Science 16 (2008): 49-57). (Year: 2008).*
Mohamed et al. (In Vitro Cellular & Developmental Biology—Plant 40.3 (2004): 284-289). (Year: 2004).*

* cited by examiner

*Primary Examiner* — Charles Logsdon
(74) *Attorney, Agent, or Firm* — Harita S. Achanta

(57) ABSTRACT

The present invention provides medium compositions and methods for the regeneration of the whole plant from explants obtained from plants belonging to the Malvaceae family, particularly the *Abelmoschus* genus, more preferably *Abelmoschus esculentus* L, through somatic embryogenesis. The present invention also provides an efficient methodology for genetic transformation of plants belonging to the Malvaceae family through somatic embryogenesis in semi-solid culture with the use of the *Agrobacterium*. The present invention is also related to a method for the development of virus-resistant transgenic plants belonging to the Malvaceae family.

1 Claim, 7 Drawing Sheets

FIG. 1. Stages of Regeneration of Okra through Somatic Embryogenesis

FIG. 2. Different Stages of Embryos, and their development
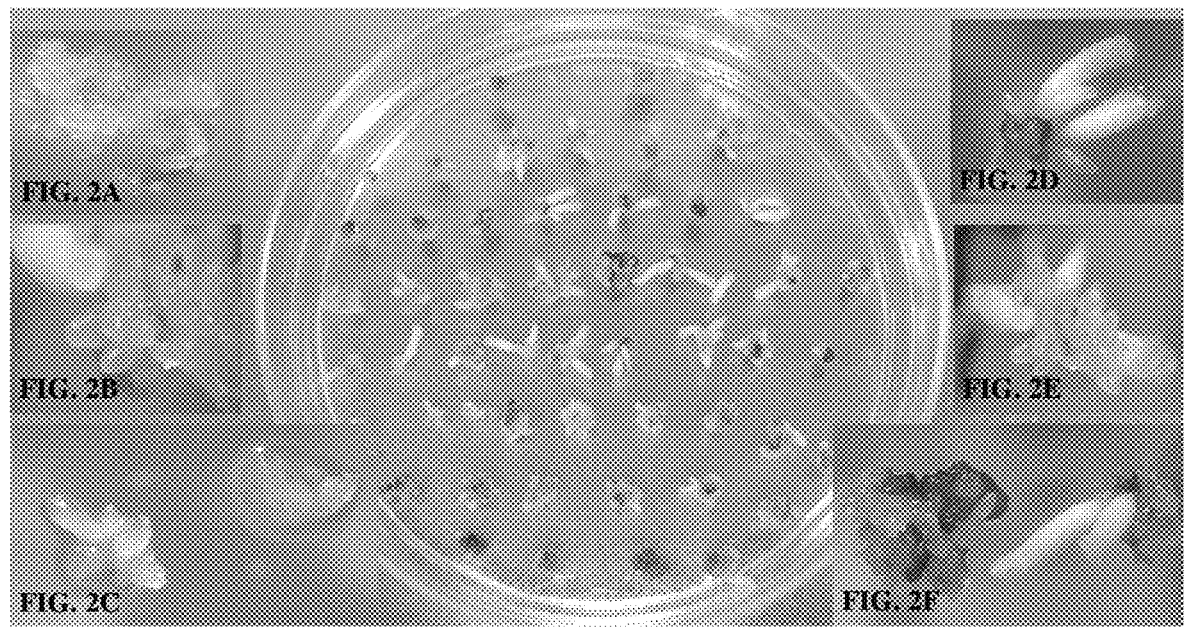

FIG. 3. Stages of Genetic Transformation and Development of Transgenic Okra with Yellow Vein Mosaic Virus resistance through Somatic Embryogenesis

FIG. 4A. Table 1
Stock Solutions for MS medium (Murashige and Skoog, 1962)

| MS Major stock: | (10X) |
|---|---|
| | Qty./500 ml |
| Ammonium nitrate ($NH_4NO_3$) | 8.25 g |
| Potassium Nitrate ($KNO_3$) | 9.50 g |
| Magnesium Sulphate ($MgSO_4.7H_2O$) | 1.85 g |
| Potassium dihydrogen phosphate ($KH_2PO_4$) | 0.85 g |

*(Dissolve the above components in about 400 ml distilled water and make up the volume up to 500 ml with distilled water and sterilize and store at 4°C)*

| MS Minor I stock: | (100 X) |
|---|---|
| | Qty./100 ml |
| Potassium Iodide (KI) | 8.30 mg |

*(Dissolve the above component in about 80 ml distilled water and make up the volume up to 100 ml with distilled water and sterilize and store at 4°C)*

| MS Minor II stock: | (50 X) |
|---|---|
| | Qty./250 ml |
| Boric Acid ($H_3BO_3$) | 077.50 mg |
| ManganousSulphate ($MnSO_4.7H_2O$) | 278.75 mg |
| If it is ($MnSO_4. H_2O$) | 236.00 mg |
| Zinc Sulphate ($ZnSO_4.7H_2O$) | 107.50 mg |

*(Dissolve the above components in about 200 ml distilled water and make up the volume up to 250 ml with distilled water and sterilize and store at 4°C)*

| MS Minor III stock: | (100 X) |
|---|---|
| | Qty. /250ml |
| Sodium Molybdate ($Na_2MO_4.7H_2O$) | 6.250 mg |
| Copper Sulphate ($CuSO_4. 5H_2O$) | 0.625 mg |
| Cobaltous Chloride ($COCl_2. 6H_2O$) | 0.625 mg |

*(Dissolve the above components in about 200 ml distilled water and make up the volume up to 250 ml with distilled water and sterilize and store at 4°C)*

| MS Iron EDTA stock: | (100 X) |
|---|---|
| | Qty. /500ml |
| A) Ferrous Sulphate ($FeSO_4.7H_2O$) | 1.398 g |
| B) EDTA di sodium ($Na_2$ EDTA) | 1.865g |

*(Sample A and B to be prepared seperately by dissolving in about 200 ml distilled water and volume made up to 250 ml; and A (250 ml) to be mixed with B (250 ml) fresh; then sterilize and store at 4°C)*

| B5 Vitamins stock: (Gamborg et al., 1968) | (100 X) |
|---|---|
| | Qty. /500ml |
| Nicotinic Acid | 0.05 g |
| Pyridoxine HCL | 0.05 g |
| Thiamine HCL | 0.50 g |
| Myo-Inositol | 5.00 g |

*(Dissolve the above components in about 400 ml distilled water and make up the volume up to 500 ml with distilled water and sterilize and store at 4°C)*

FIG. 4B. Table 2. Components for MS medium

*Quantity required to prepare 1 liter MS medium is given below*

| Components | Full strength | Half strength |
| --- | --- | --- |
| MS Major stock (10X) | 100 ml | 50 ml |
| MS Minor I stock (100X) | 10 ml | 5 ml |
| MS Minor II stock (50X) | 20 ml | 10 ml |
| MS Minor III stock (100X) | 10 ml | 5 ml |
| MS Iron EDTA stock (100X) | 10 ml | 5 ml |
| B5 Vitamins (100X) | 10 ml | 5 ml |
| Calcium Chloride ($CaCl_2 \cdot 2H_2O$) | 440 mg | 220 mg |
| Sucrose | 30 g | 15 g |

FIG. 5A. Table 3
Stock Solutions for Stewart Embryo Germination medium (Stewart, 1977)

| S Major stock: | (50X) |
|---|---|
| | Qty./500 ml |
| Ammonium nitrate (NH$_4$NO$_3$) | 6g |
| Potassium Nitrate (KNO$_3$) | 12.7 g |
| Magnesium Sulphate (MgSO$_4$.7H$_2$O) | 12.3 g |
| Potassium dihydrogen phosphate (KH$_2$PO$_4$) | 0.7 g |

*(Dissolve the above components in about 400 ml distilled water and make up the volume up to 500 ml with distilled water and sterilize and store at 4°C)*

| S Minor I stock: | (100 X) |
|---|---|
| | Qty./500 ml |
| Potassium Iodide (KI) | 12.45 mg |

*(Dissolve the above component in about 400 ml distilled water and make up the volume up to 500 ml with distilled water and sterilize and store at 4°C)*

| S Minor II stock: | (100 X) |
|---|---|
| | Qty./500 ml |
| Boric Acid (H$_3$BO$_3$) | 92.75 mg |
| Manganoussulphate (MnSO$_4$.H$_2$O) | 253.50 mg |
| Zinc Sulphate (ZnSO$_4$.7H$_2$O) | 129.39 mg |

*(Dissolve the above components in about 400 ml distilled water and make up the volume up to 500 ml with distilled water and sterilize and store at 4°C)*

| S Minor III stock: | (100 X) |
|---|---|
| | Qty. /500ml |
| Sodium Molybdate (Na$_2$MO$_4$.7H$_2$O) | 10.89 mg |
| Copper Sulphate (CuSO$_4$.5H$_2$O) | 0.37 mg |
| Cobaltous Chloride (COCl$_2$.6H$_2$O) | 0.36 mg |

*(Dissolve the above components in about 400 ml distilled water and make up the volume up to 500 ml with distilled water and sterilize and store at 4°C)*

| S Iron EDTA stock: | (100 X) |
|---|---|
| | Qty. /500ml |
| A) Ferrous Sulphate (FeSO$_4$.7H$_2$O) | 208.50 mg |
| B) EDTA di sodium (Na$_2$ EDTA) | 279.18 mg |

*(Sample A and B to be prepared seperately by dissolving in about 400 ml distilled water and volume made up to 500 ml; and A (250 ml) to be mixed with B (250 ml) fresh; then sterilize and store at 4°C)*

| Stewart's Vitamins stock: | (100 X) |
|---|---|
| | Qty. /500ml |
| Nicotinic Acid | 24.62 mg |
| Pyridoxine HCL | 41.13 mg |
| Thiamine HCL | 67.45 mg |

*(Dissolve the above components in about 400 ml distilled water and make up the volume up to 500 ml with distilled water and sterilize and store at 4°C)*

FIG. 5B. Table 4. Components for Stewart's medium

*Quantity required to prepare 1 liter Stewart's Medium is given below*

| Components | Full strength | Half strength |
|---|---|---|
| S Major stock (50X) | 20 ml | 10 ml |
| S Minor I stock (100X) | 10 ml | 5 ml |
| S Minor II stock (100X) | 10 ml | 5 ml |
| S Minor III stock (100X) | 10 ml | 5 ml |
| MS Iron EDTA stock (100X) | 10 ml | 5 ml |
| Stewart's Vitamins (100X) | 10 ml | 5 ml |
| Calcium Chloride ($CaCl_2 \cdot 2H_2O$) | 133.2 mg | 66.75 mg |
| Sucrose | 5 g | 2.5 g | ns
REGENERATION AND GENETIC TRANSFORMATION OF OKRA THROUGH SOMATIC EMBRYOGENESIS

CROSS-REFERENCE TO RELATED APPLICATIONS

The present application is a continuation of an International Application Number PCT/IN2016/000030, which application was filed Jan. 27, 2016, which claims the benefit of foreign priority application number 2617/CHE/2015, which application was filed in India on May 25, 2015.

FIELD OF INVENTION

The invention provides an efficient method for the regeneration of highly recalcitrant plants from the Malvaceae family, particularly suitable for the regeneration of Okra (*Abelmoschus esculentus* L.) plant through somatic embryogenesis. The present invention provides an efficient method for the genetic transformation of these plants through somatic embryogenesis for the development of transgenic plants with gene constructs for virus-resistance.

BACKGROUND OF THE INVENTION

Okra is a very important vegetable crop of tropical countries. Diseases caused by virus such as Yellow Vein Mosaic Virus (YVMV) and Enation Leaf Curl Virus (EnLCuV) are the major problems associated with Okra cultivation. Development of virus resistance through conventional breeding is difficult due to lack of sources for resistance in the available germplasm.

Development of virus resistance by incorporating virus resistant genes through genetic engineering approach is the most promising alternative. For successful genetic transformation, it is desirable to have highly efficient regeneration methodology. Somatic embryogenesis is an effective tool in genetic transformation for the successful development of a large number of transgenic plants. Okra is known as a highly recalcitrant crop for tissue culture and regeneration. The available regeneration methodologies are based on direct shoot organogenesis from explants which are not desirable for genetic transformation as this may generate high frequency of chimeras and could also be extremely laborious.

U.S. Pat. No. 8,067,673 discloses a method for the regeneration and transformation of Okra and other *Abelmoschus* species into a whole plant using *Agrobacterium*-mediated gene transfer or particle bombardment methods. Transgenic insect resistant Okra plants were generated either by marker based or marker-free systems.

U.S. Pat. No. 8,168,748 discloses transgenic plant comprising transforming plant cells using viruses and *Agrobacterium*, physicochemical methods such as electroporation, polyethylene glycol, biolistic or particle bombardment, micro injection, floral dip method and others. The transformed plant cells comprising the isolated nucleic acids result in increased resistance from viruses such as a geminivirus, a nanovirus and combinations thereof.

U.S. Pat. No. 8,697,445 B2 discloses regeneration and genetic transformation of Okra with the use of meristematic cells of plumule tip through *Agrobacterium*-mediated transformation or bombarding explants of development of transgenic plants with insect resistance.

Patent application WO2011087854 discloses a method for producing a plant that has increased resistance to a single stranded DNA (ssDNA) virus of the geminivirus family comprising transforming a polynucleotide though an expression vector into said plant.

Another patent application US20020083491 discloses a method of using geminivirus vectors for silencing of one or more endogenous genes in treated plants.

The study of the prior art shows that reported methods on regeneration and genetic transformation of Okra were based on direct organogenesis of shoots from shoot-tips, cotyledonary node, plumule tip and immature embryo-based explants.

The available regeneration methodologies are based on direct shoot organogenesis from explants which are not desirable for genetic transformation as this may generate high frequency of chimeras and could also be extremely laborious. Somatic embryogenesis is an effective tool in genetic transformation for the successful development of a large number of transgenic plants. So far Okra is considered as a highly recalcitrant crop for tissue culture and regeneration through Somatic Embryogenesis.

The current invention solves the existing problem by providing methods for regeneration and genetic transformation of Okra through somatic embryogenesis in semisolid culture. This invention also provides a method for the development of transgenic Okra plants with virus-resistant gene constructs.

SUMMARY OF THE INVENTION

The present invention provides a method of regeneration of the whole plant belonging to the Malvaceae family, particularly plants of *Abelmoschus* genus and more preferably *Abelmoschus esculentus* L, through somatic embryogenesis.

The present invention also provides a method for genetic transformation of Malvaceae plants using Okra (*Abelmoschus esculentus* L.) through somatic embryogenesis using *Agrobacterium*-mediated method through somatic embryogenesis for the development of the transgenic Okra plants with a virus-resistant gene construct such as a Yellow Vein Mosaic Virus (YVMV) resistant gene construct.

Another aspect of the present invention provides transformed Okra plants with resistance towards viruses such as Yellow Vein Mosaic Virus (YVMV) and Enation Leaf Curl Virus (EnLCuV).

Though the embodiments detail about regeneration and transformation of virus-resistant okra plants, this invention is not limited to the exemplary case and can be applicable to other plants particularly Malvaceae family.

It should be understood that alternatives for the present invention could be realized. The following discussion describes merely exemplary embodiments illustrating the principles of the present invention, the scope of which is recited in the claims. Those skilled in the art will readily recognize from the description and claims that numerous changes and modifications can be made without departing from the spirit and scope of the invention.

BRIEF DESCRIPTION OF THE SEVERAL VIEWS OF THE DRAWING

FIG. 1: Stages of Regeneration of Okra through Somatic Embryogenesis.

FIG. 2: Different Stages of Embryos, and their development:
FIG. 2A: Development of Globular Embryos in clusters;
FIG. 2B: Development of Globular/heart shaped Embryos in clusters;
FIG. 2C: Development of Embryogenic calli and Globular/heart shaped Embryos;
FIG. 2D: Different Stages of Somatic Embros in Single Cluster;
FIG. 2E: Different Stages of Somatic Embros in Single Cluster;
FIG. 2I: Development of Embryogenic Calli and Elongated Embryos Simultaneously
FIG. 3: Stages of Genetic Transformation and Development of Transgenic Okra with Virus resistance through Somatic Embryogenesis.

DESCRIPTION OF TABLES

Figures 1A, 1B, 1C, 1D:
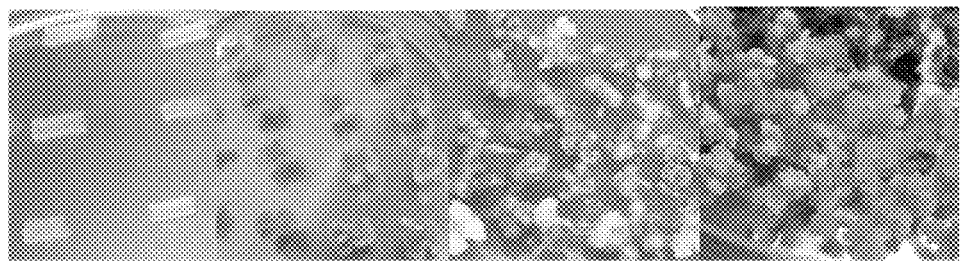
FIG. 1A: Hypocots in Callusing Medium.
FIG. 1B: Induction of calli.
FIG. 1C: Proliferation of calli.
FIG. 1D: Embryogenic calli Induction.

FIG. 4A. Table 1: Stock Solutions for MS medium (Murashige and Skoog, 1962)
FIG. 4B. Table 2: Components for MS medium
FIG. 5A. Table 3: Stock Solutions for Stewart Embryo Germination medium (Stewart, 1977)
FIG. 5B. Table 4: Components for Stewart's medium

DETAILED DESCRIPTION OF THE INVENTION

An embodiment of the present invention discloses a method of regenerating a whole plant from explants of Malvaceae family, such as plants belonging to the *Abelmoschus* species, wherein the said method comprises the steps of:
Step i) using a composition comprising media components, hormones and growth conditions for regeneration of plants through tissue culture;
Step ii) using 7-days old explants for induction of calli using specific auxin and kinetin-based medium;
Step iii) conversion of calli into embryogenic calli;
Step iv) developing large number of somatic embryos from embryogenic calli in semisolid tissue culture medium;
Step v) short time culturing of somatic embryos in tissue culture medium containing suitable hormones and media components for maturation
Step vi) Dessication of somatic embryos in desiccation medium;
Step vii) germinating matured somatic embryos into plants in basal medium containing suitable nutrients in the absence of hormones; and
Step viii) hardening and advancing the plants to subsequent generations.

Further, the invention may also provide for regeneration of plants belonging to *Abelmoschus* species wherein the plant is selected from a group comprising of *A. esculentus, A. caillei, A. ficulneus, A. crinitus, A. angulosus, A. moschatus, A. tuberculatus, A. tetraphyllus, A. manihot.*

For the current study, Okra genotypes representing proprietary lines of Rasi Seeds (P) Ltd. from a recent harvest were preferably used for standardization of the somatic embryogenesis-mediated regeneration protocol.

The said seed inoculation period is 3 to 15 days, preferably 7 days. The method of seed inoculation comprises a series of sterilization of the seeds followed by inoculation of the sterilized seeds.

Sterilization of Okra Seeds:

The Okra seeds are surface sterilized with 70% (v/v) ethanol for 1 to 30 minutes, preferably for 10 minutes and washed 3 to 4 times with sterile distilled water to remove excess ethanol. The seeds are again surface sterilized with 0.1% (w/v) aqueous mercuric chloride solution for 1 to 30 minutes, preferably for 10 minutes with continuous agitation and subsequently washed 3 to 4 times with sterile distilled water.

Inoculation of Sterilized Seeds:

Surface sterilized seeds are blot dried on sterile filter paper for a few minutes and then inoculated in culture bottles containing 30 ml of Seed Germination Medium (SGM). They are then incubated in culture bottles at temperatures ranging from 20° C. to 30° C., preferably 26° C. in darkness for 1 to 5 days, preferably for 3 days for germination; then transferred to culture room for 16:8 hour day:night photoperiod at temperatures ranging from 20° C. to 30° C., preferably 26° C. Unless specified, the tissue culture experiments are carried out in the culture room conditions initially under dark conditions. During post-somatic embryo germination, the cultures are maintained under 16:8 hours day: night photoperiod with the temperature ranging from 20° C. to 30° C., preferably 26° C. with luminosity of 1000 to 6000 lux.

Another embodiment of the present invention discloses the transfer of surface sterilized seeds onto SGM. The medium is prepared considering the requisite quantities of the components required for half-strength as provided in FIG. 4A. Table 1 and FIG. 4B. Table 2 and the volume is made up to approximately 900 ml using distilled water with the contents being uniformly dissolved. Then, the pH is adjusted to 5.6 to 5.8 using 0.1 N NaOH and the volume is made up to 1000 ml. To this, 7.0 g/L of Agar is added and sterilized using an autoclave.

Another embodiment of the present invention provides a method of regeneration of Okra plant involving explant initiation and callusing for a period of 4 weeks. The hypocots are excised out from 3 to 15 day old seedlings, preferably 7 days old aseptically grown Okra seedlings and placed in Callusing/Embryogenic Calli Induction Medium (C/ECIM) and incubated at temperature ranging from 20° C. to 30° C., preferably at 26° C. in the culture room under dark conditions (FIG. 1A). The explants are regularly subcultured at 3-4 week intervals for callus initiation and development while being maintained under dark conditions. At the cut ends of the hypocotyl explants, slimy brownish calli are induced (FIG. 1B).

Another embodiment of the present invention discloses the growth of explants in C/ECIM. C/ECIM comprises quantities of components provided in FIG. 4A. Table 1 and FIG. 4B. Table 2 supplemented with combinations of auxins in the range of 0.01 to 10 mg/L or combinations of auxin and cytokinins, with the latter in the range of 0.01 to 5 mg/L.

Another embodiment of the present invention discloses C/ECIM comprises quantities of components provided in FIG. 4A. Table 1 and FIG. 4B. Table 2, supplemented with Polyvinylpyrrolidone (PVP) in the range of 5 to 100 mg/L, preferably 25 mg/L, 2, 4-D in the range of 0.01 to 3.0 mg/L, more preferably 0.5 mg/L, and Kinetin in the range of 0.01 to 2.0 mg/l, preferably 0.1 mg/L. Then, the volume is made up to approximately 900 ml using distilled water and the contents are uniformly dissolved. Then the pH is adjusted to 5.6 to 5.8 using 0.1 N NaOH and the volume is made up to 1000 ml. To this, 3.0 g/L of phytagel is added and sterilized using an autoclave.

Another embodiment of the present invention is a method of regeneration of Okra plant wherein the duration of the embryogenic calli induction method is 8 to 20 weeks, more ideally at 12 weeks followed by subculturing of the calli once in 3-4 weeks for multiplication and proliferation in C/ECIM (FIG. 1C). This process is continued for 3 to 4 months for induction of somatic embryogenic calli (FIG. 1D). The embryogenic calli are further subcultured in the same medium at 3-4 week intervals for somatic embryogenic calli proliferation (FIG. 1D).

Another embodiment of the present invention is to provide a method of regeneration of Okra plant wherein the method of somatic embryo induction and maturation takes 15 weeks.

In yet another embodiment, the invention provides for the induction of somatic embryo followed by maturation of the embryo as indicated below.

Figures 1E, 1F, 1G:
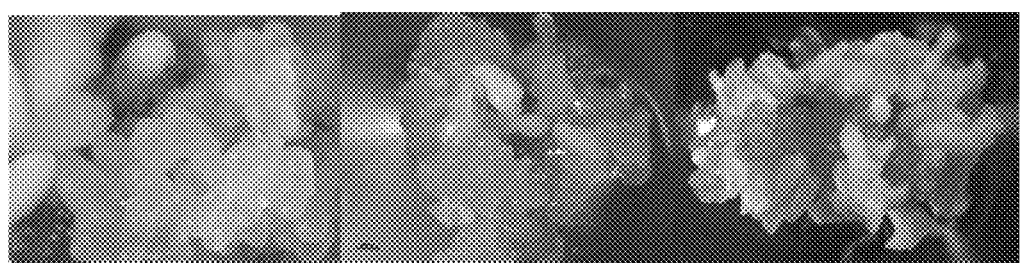
FIG. 1E: Globular Embryos Induction in clumps.
FIG. 1F: Somatic Embryo Development from Embryogenic Calli.
FIG. 1G: Somatic Embryo Clumps.

Somatic Embryo Induction:

The globular somatic embryos are induced in clusters from embryogenic calli in C/ECIM (FIG. 1E) and further developed into heart and torpedo shaped embryos. The process of embryo development in clusters and embryogenic calli proliferation occurs simultaneously (FIG. 1F and FIG. 1G; FIG. 2). Different stages of somatic embryo induction and development such as globular, heart and torpedo is given in FIG. 2.

Figures 1H, 1I, 1J:
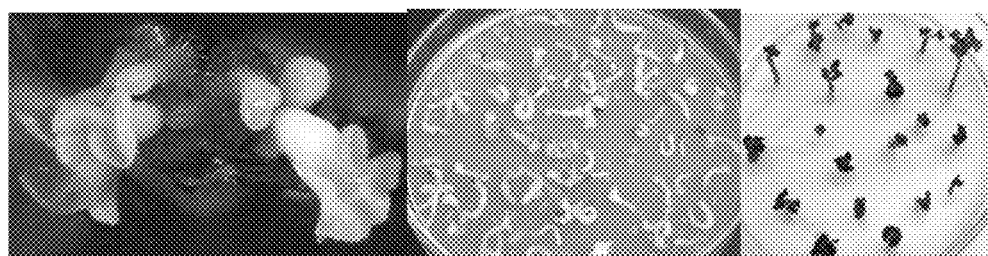
FIG. 1H: Somatic Embryos under Maturation.
FIG. 1I: Somatic Embryos under Desiccation.
FIG. 1J: Regeneration of Embryos into plants.

Embryo Maturation:

The developed embryos are separated from embryogenic calli and placed for 3 weeks in the amino acid rich medium, viz., Somatic Embryo Maturation Medium (SEMM) which allows further development and maturation as shown in FIG. 1H. After separating the embryos, the embryogenic calli are again subcultured in C/ECIM for induction of next set of embryos.

In the above embodiment, the SEMM preparation comprises the quantities of components as provided in FIG. 4A. Table 1 and FIG. 4B. Table 2 and supplemented with ABA in the range of 0.01 to 3.0 mg/L, preferably 0.5 mg/L and glutamine in the range of 1 to 1000 mg/L, preferably 50 mg/L. The volume is made up to approximately 900 ml using distilled water and the contents are uniformly dissolved. Then the pH is adjusted to 5.6 to 5.8 using 0.1 N NaOH and the volume is made up to 1000 ml. To this, 3.0 g/L of phytagel is added and sterilized using an autoclave.

Figures 1K, 1L, 1M:
FIG. 1K: Rooted plant in-vitro.
FIG. 1L: Hardening of Okra Plants in greenhouse.
FIG. 1M: Established Okra Plant in Greenhouse derived through Somatic Embryogenesis

Another embodiment of the present invention is to provide a method of regeneration of Okra plant wherein the embryo desiccation and germination into a plantlet takes 11 weeks' time. The somatic embryos are incubated for 3 weeks for elongation of embryos under dark conditions (FIG. 1I) in a desiccation medium (SEDM). Well elongated embryos are transferred to somatic embryo germinating medium (SEGM). Emerging shoots are subcultured regularly at 3 weeks interval under 16:8 hour day: night photoperiod at the temperature from 20° C. to 30° C. and more preferably at 26° C. with luminosity of 100 to 6000 lux for emergence of true leaves (FIG. 1J). The shoots are further subcultured in SEGM for the development of plants with roots (FIG. 1K).

In the above embodiment, the desiccation medium is prepared by considering the quantities of components as provided in FIG. 5A. Table 3 and FIG. 5B. Table 4, and the volume is made up to approximately 900 ml using distilled water and the contents are uniformly dissolved. Then the pH is adjusted to 6.8 using 0.1 N NaOH and the volume is made up to 1000 ml. To this, 20.0 g/L of agar is added and sterilized using an autoclave.

The somatic embryo germinating medium SEGM according to the above embodiment is prepared by considering the quantities of components required for half strength as provided in FIG. 5A. Table 3 and FIG. 5B. Table 4, and their volume is made up to approximately 900 ml using distilled water and the contents are uniformly dissolved. Then the pH is adjusted to 5.6 to 5.8 using 0.1 N NaOH and the volume is made up to 1000 ml. To this, 8.0 g/L of agar is added and sterilized using an autoclave.

Another embodiment of the present invention is to provide a method of hardening of Okra plant wherein the plantlet is transferred to the soil for further growth. Regenerated plants with few roots are hardened (2 weeks) in small plastic cups containing standard pot mixture and maintained in the plant growth chamber for 2 weeks (FIG. 1L). The established plants with well-developed roots are transplanted in soil and maintained in the greenhouse at 26±2° C. and 60% RH till the harvest of the seeds (FIG. 1M).

Still another embodiment of the present invention is to provide a method for transforming a plant belonging to the *Abelmoschus* genus such as Okra, wherein the said method comprising the steps of Step a) use of 7-days old explants for co-cultivation with *Agrobacterium;*

Step b) induction of antibiotic-resistant calli from hypocotyl segments under selection;

Step c) conversion of antibiotic-resistant calli into embryogenic calli;

Step d) development of somatic embryos from embryogenic calli in semisolid tissue culture medium;

Step e) maturation of somatic embryos and germination of matured somatic embryos into transgenic Okra plants, hardening and normal growth of regenerated transgenic plants under greenhouse conditions.

Another embodiment of the present invention is to provide a method for transforming plant belonging to the *Abelmoschus* genus such as Okra, wherein the recombinant *Agrobacterium* strain carrying DNA/RNA sequence comprises of a coding or non-coding gene sequence, inclusive or not, of terminator or promoter, as an expressing or non-expressing cassette.

In yet another embodiment of the present invention is to provide a method for transforming a plant belonging to the *Abelmoschus* genus, wherein the DNA/RNA sequences confers tolerance or resistance to viruses to transformed cells, tissues and plants.

Another embodiment of the present invention is to provide a method for the transformation of Okra through somatic embryogenesis for the development of transgenic virus-resistant Okra plants, particularly resistant towards Yellow Vein Mosaic Virus (YVMV) and Enation Leaf Curl Virus (EnLCuV).

For the current study, a method of the above embodiment comprises use of Okra genotypes representing proprietary lines of Rasi Seeds (P) Ltd. from the most recent harvest for standardization of *Agrobacterium*-mediated genetic transformation of Okra through somatic embryogenesis-mediated transformation protocol.

According to another embodiment, seed inoculation takes 2 to 15 days preferably 7 days and is carried out as described in one of the above embodiments.

Further, the invention as per the above embodiment provides a method for the preparation of the *Agrobacterium* culture. *Agrobacterium tumefaciens* (LBA4404) culture containing plasmid pGA643 harbouring virus resistant gene construct such as Replicase Antisense with selectable marker gene (nptII), is revived from −80° C. freezer glycerol stock in AB medium containing appropriate antibiotics. The culture is incubated at 28° C. under dark conditions for 2-3 days. *Agrobacterium* suspension is prepared by setting up overnight cultures by inoculating loopful of 3-day grown *Agrobacterium* culture in 50 ml of AB medium with appropriate antibiotics and incubating at 28° C. while shaking vigorously at 220 rpm. The culture is allowed to grow to obtain $OD_{600}$ of 0.8. The overnight grown culture is diluted to an $OD_{600}$ of 0.3. The diluted culture is incubated on a shaker at 28° C. with 220 rpm for 3 to 4 hours to obtain $OD_{600}$ of 0.6. The culture is resuspended in MS based liquid medium for co-cultivation. Acetosyringone suspended in DMSO is added to a final concentration of 100 μM to diluted *Agrobacterium* culture prior to co-cultivation.

Figures 3A, 3B, 3C, 3D:
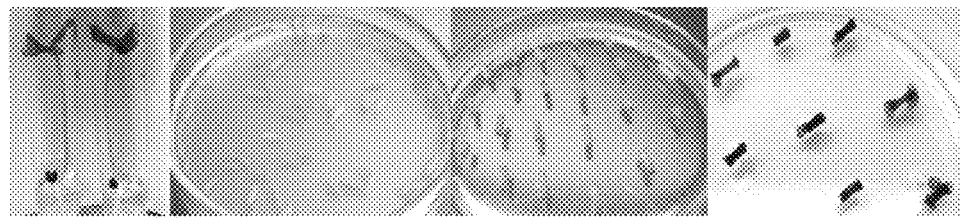
FIG. 3A: 7 days old seedlings.
FIG. 3B: Hypocots under co-cultivation.
FIG. 3C : Hypocots under selection.
FIG. 3D : Callus induction under selection.

Another embodiment of the present invention is to provide methods for explant initiation following cocultivation, explants are excised out from 2 to 15 days old Okra seedlings, preferably 7 days old aseptically grown Okra seedlings (FIG. 3A) and placed in sterile petri dishes. *Agrobacterium* suspension is added to the explant segments and mixed well which is followed by incubation for 2 to 90 minutes more preferably 30 minutes (FIG. 3B). *Agrobacterium* suspension is removed through aspiration and explants are allowed for air drying for brief time. The explants are placed in Co-cultivation Medium (CCM) and incubated at the temperature from 20° C. to 30° C., more preferably at 26° C. in the culture room under dark conditions for 1 to 7 days, preferably 3 days (FIG. 3C).

As per the above embodiment, the said medium CCM, comprises quantities of components as provided in FIG. 4A. Table 1 and FIG. 4B. Table 2 and supplemented with 2,4-D in the range of 0.01 to 3.0 mg/L, preferably 0.5 mg/L, and Kinetin in the range of 0.01 to 2.0 mg/l, preferably 0.1 mg/L. Then, the volume is made up to approximately 900 ml using distilled water and the contents are uniformly dissolved. Then the pH is adjusted to 5.6 to 5.8 using 0.1 N NaOH. Then the volume is made up to 1000 ml. To this, 3.0 g/L of phytagel is added and sterilized using an autoclave. Acetosyringone is added to the sterilized medium to a final concentration of 100 μM. Then, the medium is dispensed in sterile petri plates under sterile conditions.

The explants from the above embodiment are co-cultivated explants that are blot dried to remove excess *Agrobacterium* and placed in C/ECIM supplemented with Geneticin in the range of 0.1 to 100 mg/L, preferably 25 mg/L and Cefotaxime in the range of 10 to 1000 mg/L, preferably 300 mg/L. They are then incubated at the temperature from 20° C. to 30° C. and more preferably at 26° C. in the culture room under dark conditions for 3-4 weeks for induction of antibiotic resistant calli (FIG. 3D). The antibiotic resistant calli are carefully excised from explants and subcultured twice at 3 to 4 week intervals in the same medium for the multiplication of antibiotic resistant calli.

Figures 3E, 3F, 3G, 3H:
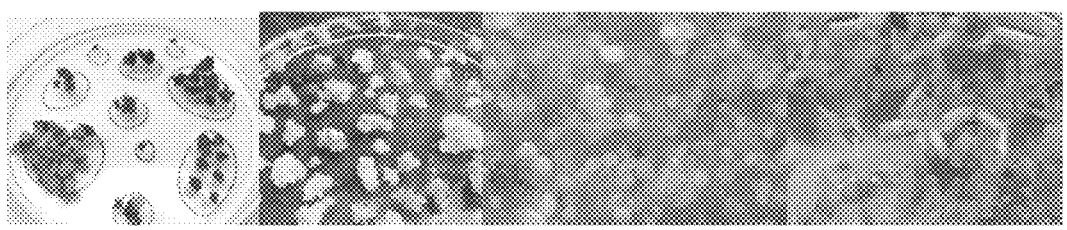
FIG. 3E : Independent calli lines in selection.
FIG. 3F : Embryogenic calli induction.
FIG. 3G : Induction of globular somatic embryos in clusters.
FIG. 3H : Embryos development.

Another embodiment of the present invention provides a method for embryogenic calli induction which comprises subculturing the antibiotic resistant calli once in 3 to 4 weeks for calli multiplication and proliferation in C/ECIM (FIG. 3E). This process is continued for 3 to 4 months for the induction of somatic embryogenic calli. The embryogenic calli are further subcultured in the same medium at 3 to 4 week intervals for somatic embryogenic calli proliferation (FIG. 3F).

Figures 3I, 3J, 3K, 3L:
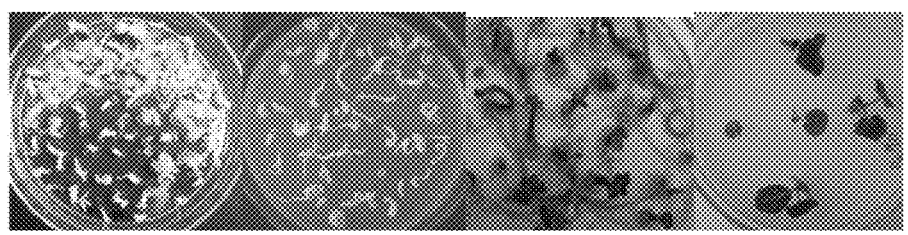
FIG. 3I : Somatic embryo maturation.
FIG. 3J : Somatic embryo desiccation.
FIG. 3K : Germination of somatic embryos.
FIG. 3L : Shoot development.

Still another embodiment of the present invention provides a method for somatic embryo induction and maturation comprising the induction of globular somatic embryos in clusters from embryogenic calli in C/ECIM (FIG. 3G) and further development into heart and torpedo shaped embryos (FIG. 3H). The developed embryos are separated from embryogenic calli and placed in the amino acid rich medium SEMM for 3 weeks (FIG. 3I). After separating the embryos, the embryogenic calli are again subcultured in C/ECIM for induction of the next set of embryos.

Figures 3M, 3N, 3O, 3P:
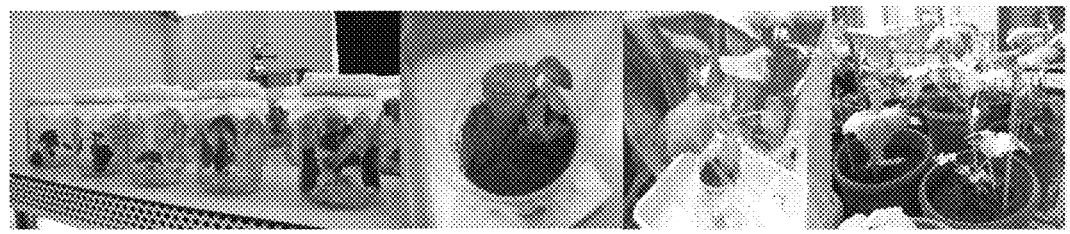
FIG. 3M: Regenerated transgenic plants with roots.
FIG. 3N : Hardening of transgenic okra plant.
FIG. 3O : Transgenic plant in Growth chamber.
FIG. 3P : Transgenic plants in Greenhouse

Further, the invention provides a method for desiccation and germination of the embryo into a plantlet which comprises transfer of somatic embryos to desiccation medium SEDM (FIG. 3J) and incubation for 3 weeks for elongation of embryos under dark conditions. Well-elongated embryos are transferred to the somatic embryo germinating medium SEGM supplemented with Geneticin in the range of 0.1 to 100 mg/L, preferably between 15 mg/L (FIG. 3K). The emerging shoots are subcultured regularly at 3 weeks interval under 16:8 hr day: night photoperiod at the temperature 20° C. to 30° C. and more preferably at 26° C. for the emergence of true leaves (FIG. 3L). The shoots are further subcultured in SEGM supplemented with Geneticin in the range of 0.1 to 100 mg/L, preferably between 15 mg/L for the development of transgenic plants with roots (FIG. 3M).

Another embodiment of the present invention provides a method for the hardening of the transformed plants obtained from the previous embodiment. Regenerated transgenic plants with few roots are hardened in small plastic cups containing standard pot mixture (FIG. 3N) and maintained in the plant growth chamber for 2 weeks (FIG. 3O). Established transgenic plants with well-developed roots are then transplanted and maintained in the greenhouse at 28±2° C. and 60% RH for molecular studies and harvest of seeds (FIG. 3P).

The present invention provides plant regeneration from a variety of explants, the explants selected from a group comprising of cotyledons with petiole, hypocotyls, embryo, immature embryo, leaf lamina, cotyledonary axil, shoot tip, anther, root, callus or other suitable explants of Okra or *Abelmoschus* genus. Regeneration through somatic embryogenesis in semisolid culture results in high frequency of Okra plant regeneration. Genetic transformation of Okra through somatic embryogenesis will eventually lead to the development of Okra plants with desirable virus resistance.

It is understood that the examples and embodiments described herein are for illustrative purposes only and that various modifications or changes in light thereof are to be included within the spirit and purview of this application and scope of the appended claims.

The invention claimed is:

1. A method for fostering somatic embryogenesis-mediated regeneration of a plant belonging to an *Abelmoschus* species, comprising:
   i. forming calli by culturing hypocotyl segment explants from an *Abelmoschus* species plant on or in Callusing/Embryogenic Calli Induction Medium (C/ECIM) comprising MS based medium supplemented with 25 mg/L Polyvinylpyrrolidone (PVP) and a combination of an auxin 2,4-D and a cytokinin Kinetin, in a ratio of 5:1 by weight;
   ii. developing embryogenic calli and forming somatic embryos from the embryogenic calli by further culturing the calli formed in part (i) in Callusing/Embryogenic Calli Induction Medium (C/ECIM) comprising MS based medium supplemented with 25 mg/L Polyvinylpyrrolidone (PVP) and a combination of an auxin 2,4-D and a cytokinin Kinetin, in a ratio of 5:1 by weight;
   (iii) culturing the somatic embryos formed in part (ii) for at least three weeks in Somatic Embryo Maturation Medium (SEMM) comprising MS based medium supplemented with Abscisic acid (ABA) and glutamine in a ratio of 0.5:50.0 mg/L for embryo maturation;
   iv. culturing the matured somatic embryos of part (iii) in a desiccation medium comprising Stewart's medium supplemented with 20.0 g/L of agar;
   v. germinating the somatic embryos of part (iv) into plants in Somatic Embryo Germinating Medium (SEGM) comprising of Stewart's medium excluding hormones; and
   vi. hardening the plants of part (v) and allowing further growth of plants under Greenhouse conditions.

* * * * *